United States Patent
Connery et al.

(10) Patent No.: US 11,449,830 B2
(45) Date of Patent: Sep. 20, 2022

(54) SECURE METHOD FOR HEALTH RECORD TRANSMISSION TO EMERGENCY SERVICE PERSONNEL

(71) Applicant: IQVIA Inc., Parsippany, NJ (US)

(72) Inventors: Glenn Connery, Southampton, PA (US); Matthew Tindall, Jersey City, NJ (US); Scott Hanslip, Newtown, PA (US)

(73) Assignee: IQVIA Inc., Parsippany, NJ (US)

( * ) Notice: Subject to any disclaimer, the term of this patent is extended or adjusted under 35 U.S.C. 154(b) by 1048 days.

(21) Appl. No.: 15/433,061

(22) Filed: Feb. 15, 2017

(65) Prior Publication Data

US 2017/0161438 A1 Jun. 8, 2017

Related U.S. Application Data

(63) Continuation of application No. 14/048,273, filed on Oct. 8, 2013, now abandoned.

(51) Int. Cl.
| | |
|---|---|
| *G06Q 10/10* | (2012.01) |
| *G16H 10/60* | (2018.01) |
| *G16H 40/67* | (2018.01) |
| *B60R 21/00* | (2006.01) |

(52) U.S. Cl.
CPC .......... *G06Q 10/10* (2013.01); *B60R 21/00* (2013.01); *G16H 10/60* (2018.01); *G16H 40/67* (2018.01); *B60R 2021/0027* (2013.01)

(58) Field of Classification Search
None
See application file for complete search history.

(56) References Cited

U.S. PATENT DOCUMENTS

| 8,219,299 B2 * | 7/2012 | Thiel ................. B60W 30/143 |
| | | 340/435 |
| 8,464,046 B1 | 6/2013 | Kragh |
| 2002/0103622 A1 | 8/2002 | Burge |

(Continued)

FOREIGN PATENT DOCUMENTS

| CN | 101755436 | 6/2010 |
| CN | 102546169 | 7/2012 |

(Continued)

OTHER PUBLICATIONS

K. Lorincz et al., "Sensor networks for emergency response: challenges and opportunities," in IEEE Pervasive Computing, vol. 3, No. 4, pp. 16-23, Oct.-Dec. 2004. (Year: 2004).*

(Continued)

*Primary Examiner* — Lena Najarian
(74) *Attorney, Agent, or Firm* — Fish & Richardson P.C.

(57) ABSTRACT

An indication that an occupant has entered a vehicle is detected on a computing device. The occupant is identified based on the indication that the occupant has entered the vehicle. A health record that is associated with the occupant is accessed by the computing device. The computing device enables the accessed health record associated with the occupant to be available from a secure digital storage container. The health record associated with the occupant is provided to a second computing device registered to a first responder from the secure digital storage container based on detecting an indication that the vehicle has had a collision.

17 Claims, 7 Drawing Sheets

(56) References Cited

U.S. PATENT DOCUMENTS

| | | | |
|---|---|---|---|
| 2004/0133082 A1* | 7/2004 | Abraham-Fuchs | A61B 5/6887 600/300 |
| 2005/0107673 A1 | 5/2005 | Ball | |
| 2006/0180647 A1 | 8/2006 | Hansen | |
| 2008/0166992 A1 | 7/2008 | Ricordi et al. | |
| 2008/0268808 A1* | 10/2008 | Gray | H04W 4/029 455/404.2 |
| 2008/0297341 A1 | 12/2008 | McClanahan | |
| 2008/0319794 A1 | 12/2008 | Carlson | |
| 2009/0064295 A1* | 3/2009 | Budampati | H04W 12/0802 726/6 |
| 2009/0198733 A1 | 8/2009 | Gounares | |

FOREIGN PATENT DOCUMENTS

| | | |
|---|---|---|
| EP | 1770572 | 4/2007 |
| JP | 2001141466 | 5/2001 |
| JP | 2002312492 | 10/2002 |
| JP | 2003162578 | 6/2003 |
| JP | 2004-139423 | 5/2004 |
| JP | 2004139426 | 5/2004 |
| JP | 2006201998 | 8/2006 |
| JP | 2006-277379 | 10/2006 |
| JP | 2006302206 | 11/2006 |
| JP | 2007094935 | 4/2007 |
| JP | 2008269239 | 11/2008 |
| JP | 2009244078 | 10/2009 |
| JP | 2009254544 | 11/2009 |
| JP | 2011146756 | 7/2011 |
| JP | 2012-088809 | 5/2012 |
| JP | 2013008347 | 1/2013 |
| WO | WO2006075419 | 7/2006 |

OTHER PUBLICATIONS

JP Office Action issued in Japanese Application No. 2014-206646, dated Jul. 30, 2018, 10 pages.
European Search Report European Patent Appln No. 19205149.8, dated Feb. 19, 2020, 10 pages.
European Search Report dated Jul. 30, 2019 from European Patent Application No. 14187903.1, 8 pages.
JP Office Action in Japanese Application No. 2019-120150, dated Jul. 27, 2020, 12 pages.
KR Office Action in Korean Application No. 10-2014-0136014, dated Jul. 28, 2020, 7 pages.
Capzule.com PHR [online], "Your Family Health Data in One App. (Personal Medical/Health Records)," available on or before Nov. 3, 2014, via internet archive: Wayback Machine URL <https://web.archive.org/web/20141103164403/http://www.capzule.com:80/phr>, URL<http://capzule.com/phr/>, 4 pages.
EP Search Report in European Application No. 14187903.1, dated Jun. 19, 2015, 8 pages.
Suzuki et al., "Demonstrative experiment of personal health record system using public account for personal information management," IEICE Technical Report, Nov. 2010, 110(282): 7 pages (abstract only).

* cited by examiner

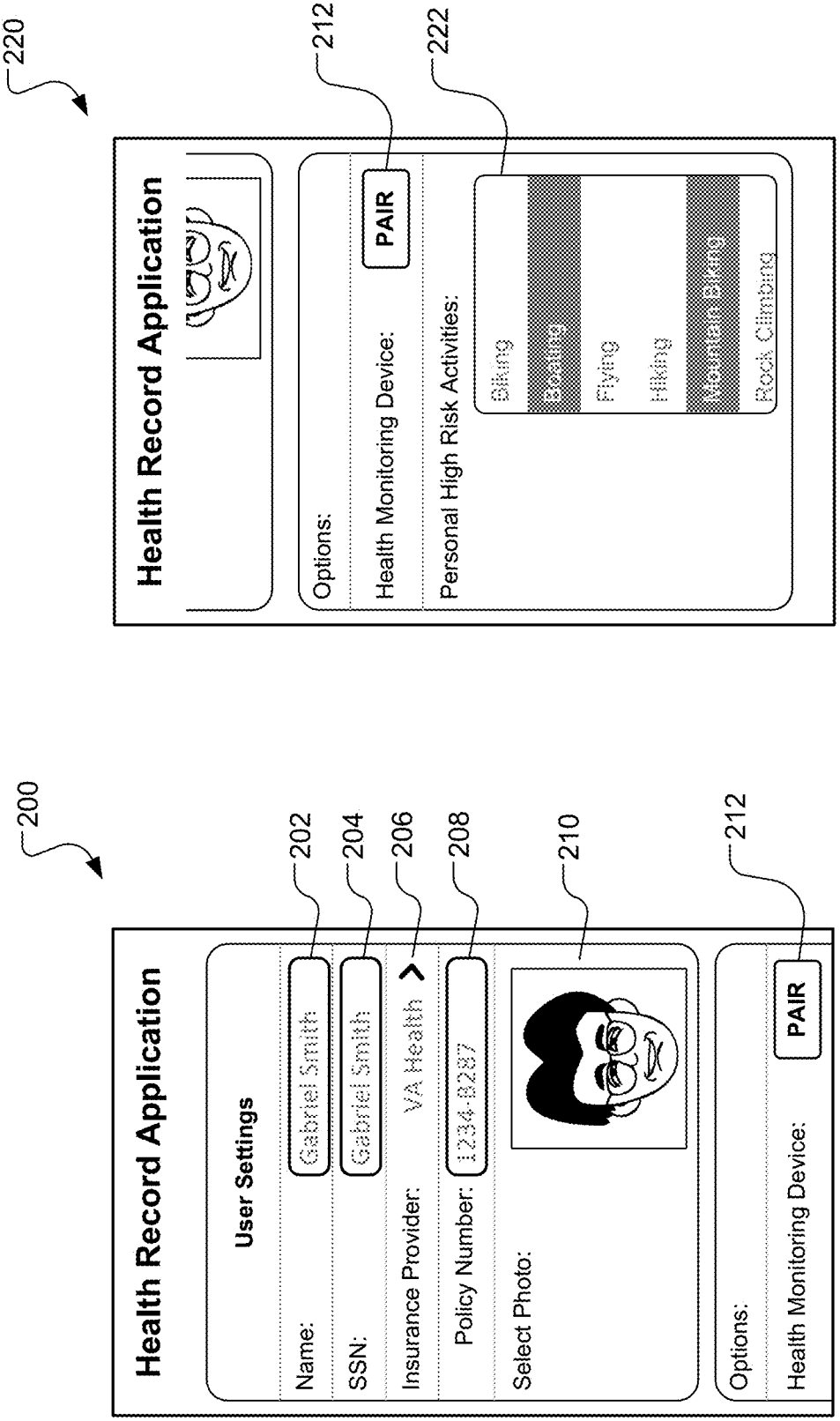

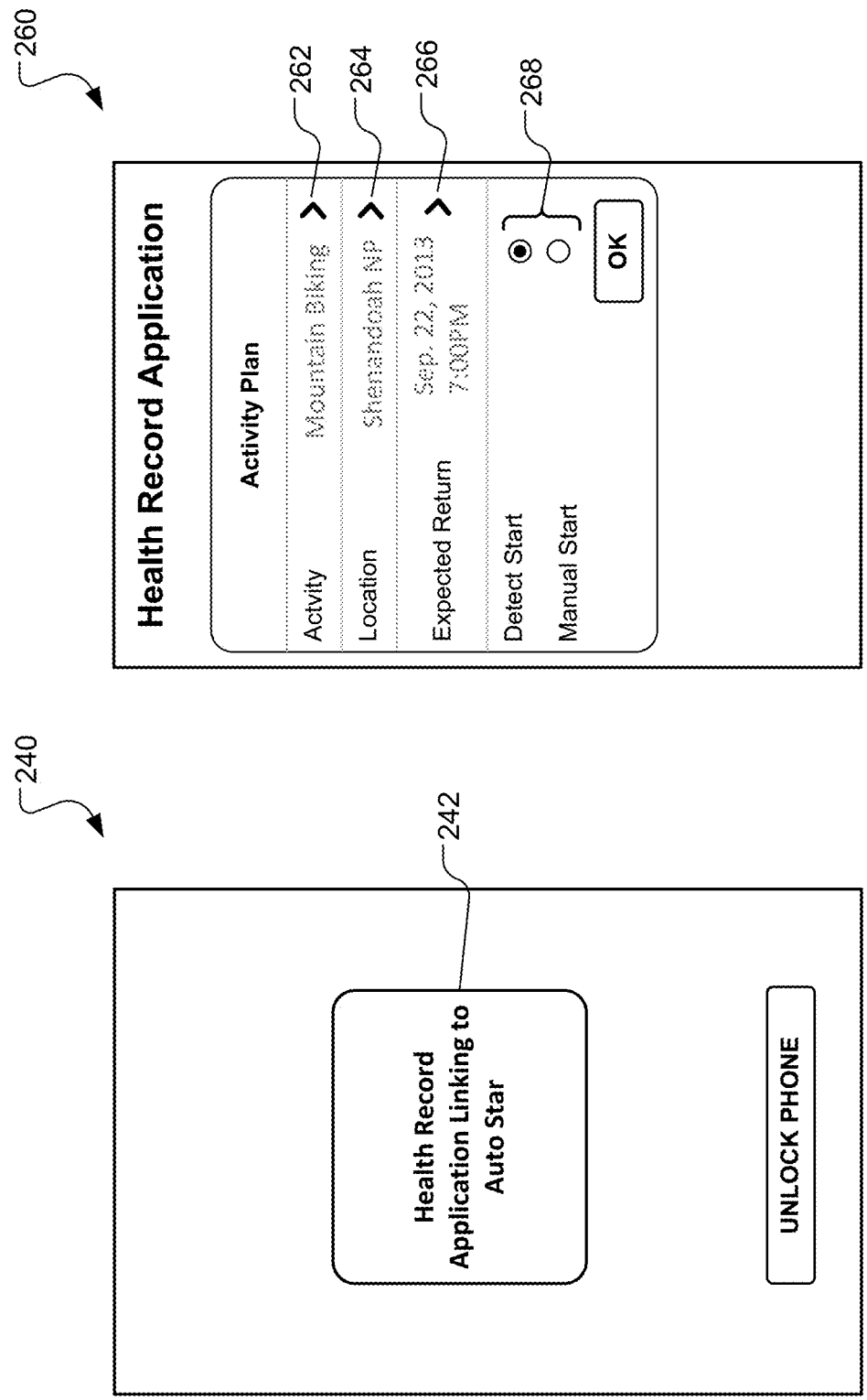

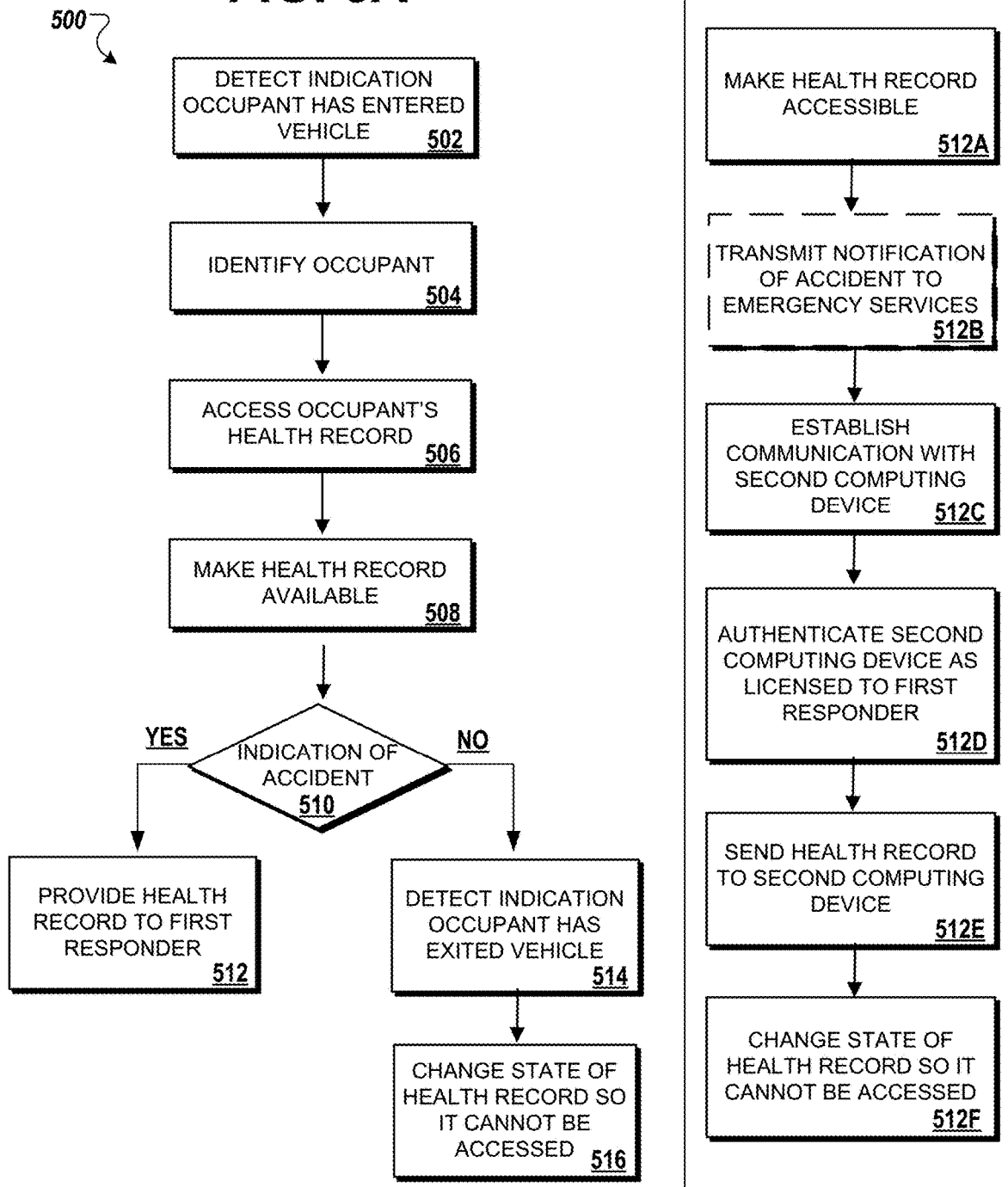

SECURE METHOD FOR HEALTH RECORD TRANSMISSION TO EMERGENCY SERVICE PERSONNEL

CROSS-REFERENCE TO RELATED APPLICATION(S)

This application is a continuation of U.S. patent application Ser. No. 14/048,273, filed Oct. 8, 2013, the contents of which are incorporated by reference in its entirety.

TECHNICAL FIELD

This specification relates to providing emergency services personnel with on scene access to a victim's medical information.

BACKGROUND

In certain circumstances, an accident victim may be unable to provide pertinent details about his or her medical history to emergency service personnel. They may be unconscious or in shock from the accident.

SUMMARY

In an aspect, an indication that an occupant has entered a vehicle is detected on a computing device. The occupant is identified based on the detected indication that the occupant has entered the vehicle. A health record that is associated with the occupant is accessed by the computing device. The computing device enables the accessed health record associated with the occupant to be available from a secure digital storage container. The state of the health record in the secure digital storage container is changed such that it cannot be accessed based on detecting an indication that the occupant has exited the vehicle.

In another aspect, an indication that an occupant has entered a vehicle is detected on a computing device. The occupant is identified based on the indication that the occupant has entered the vehicle. A health record that is associated with the occupant is accessed by the computing device. The computing device enables the accessed health record associated with the occupant to be available from a secure digital storage container. The health record associated with the occupant is provided to a second computing device registered to a first responder from the secure digital storage container based on detecting an indication that the vehicle has had a collision.

Implementations may include one or more of the following features. For example, the computing device may include a wireless mobile computing device. The computing device may include a vehicle computer. Enabling the accessed health record associated with the occupant to be available from a secure digital storage container may include enabling the accessed health record associated with the occupant to be available from a secure digital storage container on the computing device. Enabling the accessed health record associated with the occupant to be available from a secure digital storage container may include enabling the accessed health record associated with the occupant to be available from a cloud-based secure digital storage container.

Detecting an indication that an occupant has entered a vehicle may include performing near field communication with a mobile computing device, and identifying the occupant based on the indication that the occupant has entered the vehicle may include receiving identification information from the mobile computing device. Changing the state of the health record in the secure digital storage container such that it cannot be accessed based on detecting an indication that the occupant has exited the vehicle may include changing the state of the health record in the secure digital storage container such that it cannot be accessed based on detecting an indication that a distance between the computing device and the mobile computing device has exceeded a threshold value.

Changing the state of the health record in the secure digital storage container such that it cannot be accessed based on detecting an indication that the occupant has exited the vehicle may include changing the state of the health record in the secure digital storage container such that it cannot be accessed based on detecting an indication that the computing device has lost near field communications with the mobile computing device. Enabling the accessed health record associated with the occupant to be available from the secure digital storage container may include enabling the accessed health record associated with the occupant and a photograph of the occupant to be available from the secure digital storage container.

Providing the health record associated with the occupant to the first responder from the secure digital storage container based on detecting an indication that the vehicle has had the collision may include providing the health record associated with the occupant accessible to the first responder from the secure digital storage container based on detecting an indication that an airbag in the vehicle has deployed.

Providing the health record associated with the occupant to the first responder from the secure digital storage container based on detecting an indication that the vehicle has had the collision may include providing the health record associated with the occupant to a second computing device from the secure digital storage container based on detecting an indication that the vehicle has had the collision, where the second computing device is identified as licensed to the first responder.

Based on detecting an indication that the vehicle has had the collision, the computing device may make the health record associated with the occupant accessible by the second computing device registered to the first responder from the secure digital storage container, provide the health record associated with the occupant to the second computing device registered to the first responder from the secure digital storage container, and change the state of the health record associated with the occupant in the secure digital storage container such that the health record associated with the occupant can no longer be accessed.

Changing the state of the health record associated with the occupant in the secure digital storage container such that the health record associated with the occupant can no longer be accessed may include changing the state of the health record associated with the occupant in the secure digital storage container such that the health record associated with the occupant can no longer be accessed after a predetermined period of time from detecting the indication that the vehicle has had the collision.

Providing the health record associated with the occupant to the first responder from the secure digital storage container based on detecting an indication that the vehicle has had the collision may include receiving data indicating at least one of the occupant's vital signs and providing the data indicating at least one of the occupant's vital signs to the first responder.

In yet another aspect, an indication that a user of a computing device is engaged in an activity is detected on the computing device. A health record associated with the user is made available to a first responder based detecting the indication that the user of the computing device is engaged in an activity. The state of the health record associated with the user is changed such that it cannot be accessed based on detecting an indication that the occupant is no longer engaged in the activity.

In yet another aspect, an indication that a user of a computing device is engaged in an activity may be detected on the computing device. A health record associated with the user is made available to a first responder based detecting the indication that the user of the computing device is engaged in an activity. The health record associated with the user is provided to a first responder based on detecting an indication that the user has been involved in an accident.

Implementations may include one or more of the following features. For example, the computing device may include a wireless mobile computing device. Making the health record associated with the user to be available from a secure digital storage container may include making the health record associated with the user to be available from a secure digital storage container on the computing device. Making the health record associated with the user to be available from a secure digital storage container may include making the health record associated with the user to be available from a cloud-based secure digital storage container.

Detecting an indication that a user of the computing device is engaged in an activity may include receiving a motion input and determining that the received motion input indicates that the user of the computing device is engaged in an activity. Detecting an indication that a user of the computing device is engaged in an activity may include receiving a global positioning system (GPS) input and determining that the received GPS input indicates that the user of the computing device is engaged in an activity. Changing the state of the health record associated with the user such that it cannot be accessed based on detecting an indication that the occupant is no longer engaged in the activity may include changing the state of the health record in the secure digital storage container such that it cannot be accessed based on detecting that the indication that the user of the computing device is engaged in an activity has ceased.

Changing the state of the health record associated with the user such that it cannot be accessed may include deleting the health record associated with the user. Making the health record associated with the user to be available from the secure digital storage container may include making the health record associated with the user and a photograph of the user to be available from the secure digital storage container. Providing the health record associated with the user to a first responder based on detecting an indication that the user has been involved in an accident may include providing the health record associated with the user to a first responder based on determining that a detected motion input or GPS input indicates that the user has been involved in an accident.

Providing the health record associated with the user to a first responder based on detecting an indication that the user has been involved in an accident may include providing the health record associated with the occupant to a second computing device based on detecting an indication that the user has been involved in an accident, where the second computing device being identified as licensed to the first responder. Providing the health record associated with the user to a first responder based on detecting an indication that the user has been involved in an accident may include making the health record associated with the user accessible by the second computing device registered to the first responder, providing the health record associated with the user to the second computing device registered to the first responder and changing the state of the health record associated with the user such that the health record associated with the user can no longer be accessed.

Changing the state of the health record associated with the user such that the health record associated with the user can no longer be accessed may include changing the state of the health record associated with the user such that the health record associated with the user can no longer be accessed after a predetermined period of time from detecting the indication that the user has been involved in an accident. Providing the health record associated with the user to a first responder based on detecting an indication that the user has been involved in an accident may include receiving data indicating at least one of the occupant's vital signs, and providing the data indicating at least one of the occupant's vital signs to the first responder.

The details of one or more implementation of the subject matter described in this specification are set forth in the accompanying drawings and the description below. Other potential features, aspects, and advantages of the subject matter will become apparent from the description, the drawings, and the claims.

DESCRIPTION OF DRAWINGS

FIGS. 2A-2D illustrate example graphical user interfaces (GUIs) of an example user health record application.

FIGS. 3A and 3B illustrate example GUIs of an example first responder health record application.

FIGS. 5A and 5B are flow charts of a process for providing a user's health record data to emergency service personnel.

Like reference symbols in the various drawings indicate like elements.

DETAILED DESCRIPTION

Figure 1A:
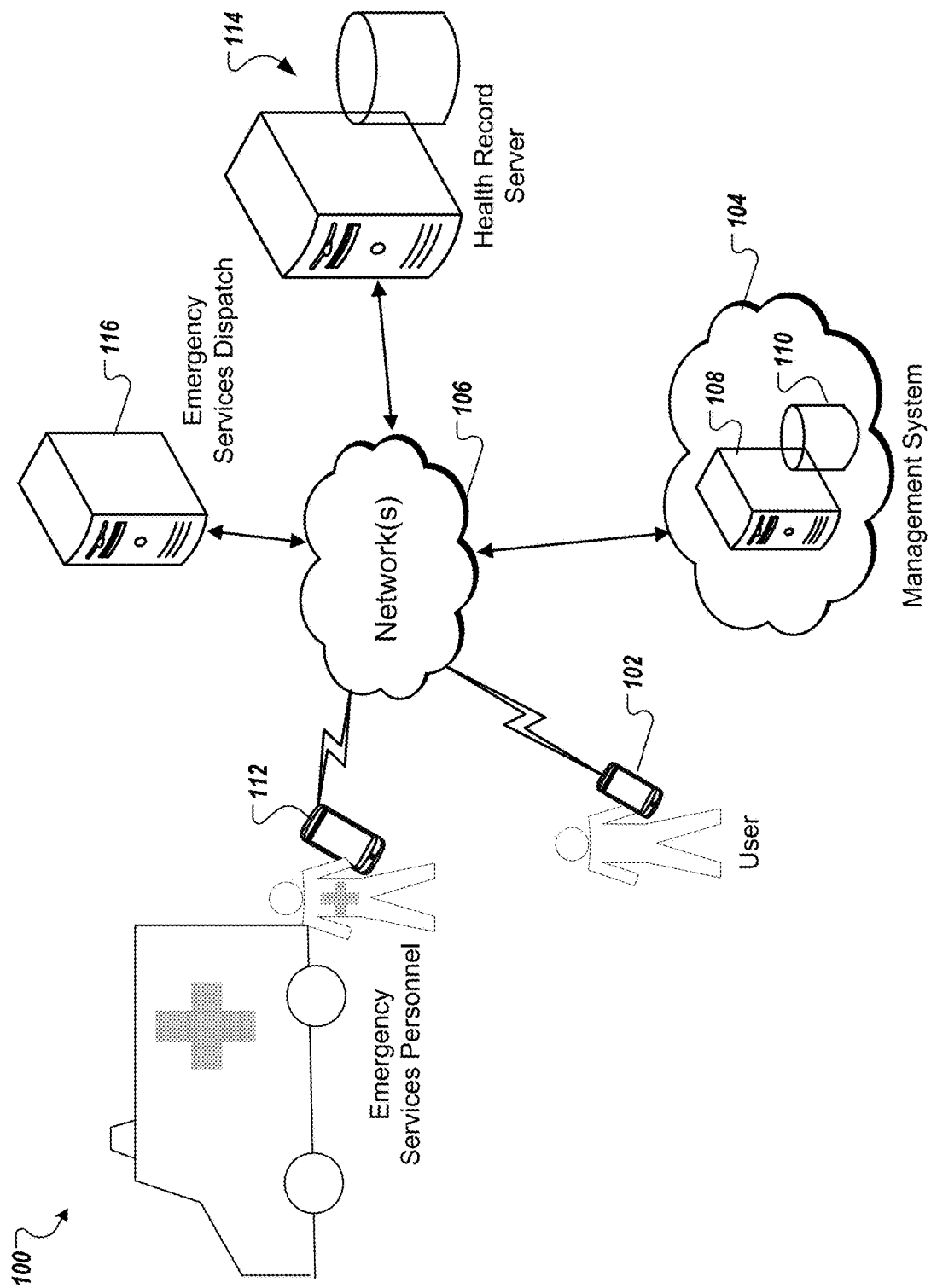
FIGS. 1A and 1B are diagrams of example systems that securely provide user health record data to emergency service personnel.

Techniques are described for securely providing an individual's health record data to emergency service personnel at or in route to the scene of an accident. The concepts described herein may provide several advantages to emergency personnel and accident victims. For example, implementations of the invention may provide a secure method for emergency personnel to access a user's health record information (e.g., pre-existing health conditions, current medications, and allergies) at the scene of an accident, while maintaining a high level of security for the user's health data and maintaining compliance with the Health Insurance Portability and Accountability Act (HIPPA). Implementations may provide emergency personnel with potentially life-saving details from the user's health history when a user is unable to provide those details due to unconsciousness, shock, head injuries, or other injuries from an accident.

An individual's computing device is configured to exchange electronic communications with other computing devices through a network (e.g., a wireless cellular network, a wireless local area network (WLAN) or Wi-Fi network, a Third Generation (3G) or Fourth Generation (4G) mobile telecommunications network), to exchange electronic communications with other computing devices using short-range wireless communication (e.g., Bluetooth or Near field communication (NFC)), and to receive input. A user health record application operating on the individual's computing device is configured to detect indications of activities performed by the individual and to detect indications that the individual was involved in an accident. Upon detecting an indication that the individual is engaged in an activity (e.g., a risky activity such as driving or riding in a vehicle or a participating in sporting activity), the user health application initiates communications with a health record management system causing the management system to make the individual's health record available to emergency service personnel. In some implementations, the user health application receives the individual's health record data and securely stores the data in a secure digital storage container on the individual's computing device. In some implementations, the user health application causes the management system to store the individual's health record data in cloud-based secure digital data storage container.

In the event that the individual is involved in an accident, the user health record application detects an indication of the accident and provides the individual's health record data to a first responder computing device operated by emergency service personnel. The user health application may communicate the individual's health record data to the first responder computing device via short-range wireless communications (e.g., Bluetooth or NFC). The first responder computing device may include an emergency service health record application that authenticates itself to the user health record application thereby ensuring communication of the individual's health record only to a properly authenticated computing device. In some implementations, the user health application enables communication of the data to a first responder computing device for a predetermined period of time after detection of the accident, and securely removes the health record data (from the individual's computing device, the cloud-based storage, or both) after the predetermined period.

In the event that the individual ceases the detected activity without being involved in an accident, the user health record application detects an indication that the user is no longer engaged in the activity and changes the state of the individual's health record data such that it cannot be accessed. In some implementations, the user health application securely removes the individual's health record data from the secure digital storage container on the individual's computing device. In some implementations, the user health application causes the management system to securely remove the individual's health record data from the cloud-based secure data storage container.

By way of example, assume a user, Ben, has installed a user health record application on his smartphone and has configured it to access his medical record data. When Ben goes on a mountain biking trip his user health record application operating on his smartphone will sense (e.g., via motion/GPS inputs) when he has begun riding his mountain bike. Based on this indication that Ben is involved in a risky activity (e.g., mountain biking), the health record application will coordinate with a health record management system via Ben's wireless cellular network provider to make his health record data readily available in the event of an accident. If Ben enjoys an accident free mountain biking trip, the health record application will sense (e.g., via the cessation of the motion inputs associated with mountain biking) that he is no longer riding his mountain bike. The user health record application then will coordinate with the health record managing system to make his health records inaccessible from the secure data storage container.

On the other hand, if Ben is involved in an accident, the user health record application will sense (e.g., via motion/GPS inputs) that Ben has been involved in an accident. The user health record application will then make Ben's health record data accessible to emergency service personnel and may both provide Ben's location to the health record management system and request emergency services. When first responders arrive, they will be able to use an emergency services version of the health record application to access Ben's health records from his smartphone (or from the health record management system in if Ben's phone is damaged in the accident).

The user health record application, thereby, provides a high-level of security for the individual's health record data by limiting the amount of time in which the data is accessible and only providing the health record information to second (first responder) computing device in the event that an accident is detected. In addition, the user health record application also provides secure way for emergency service personnel to obtain needed health record information if a victim is unable to provide such information themselves.

Figure 1B:
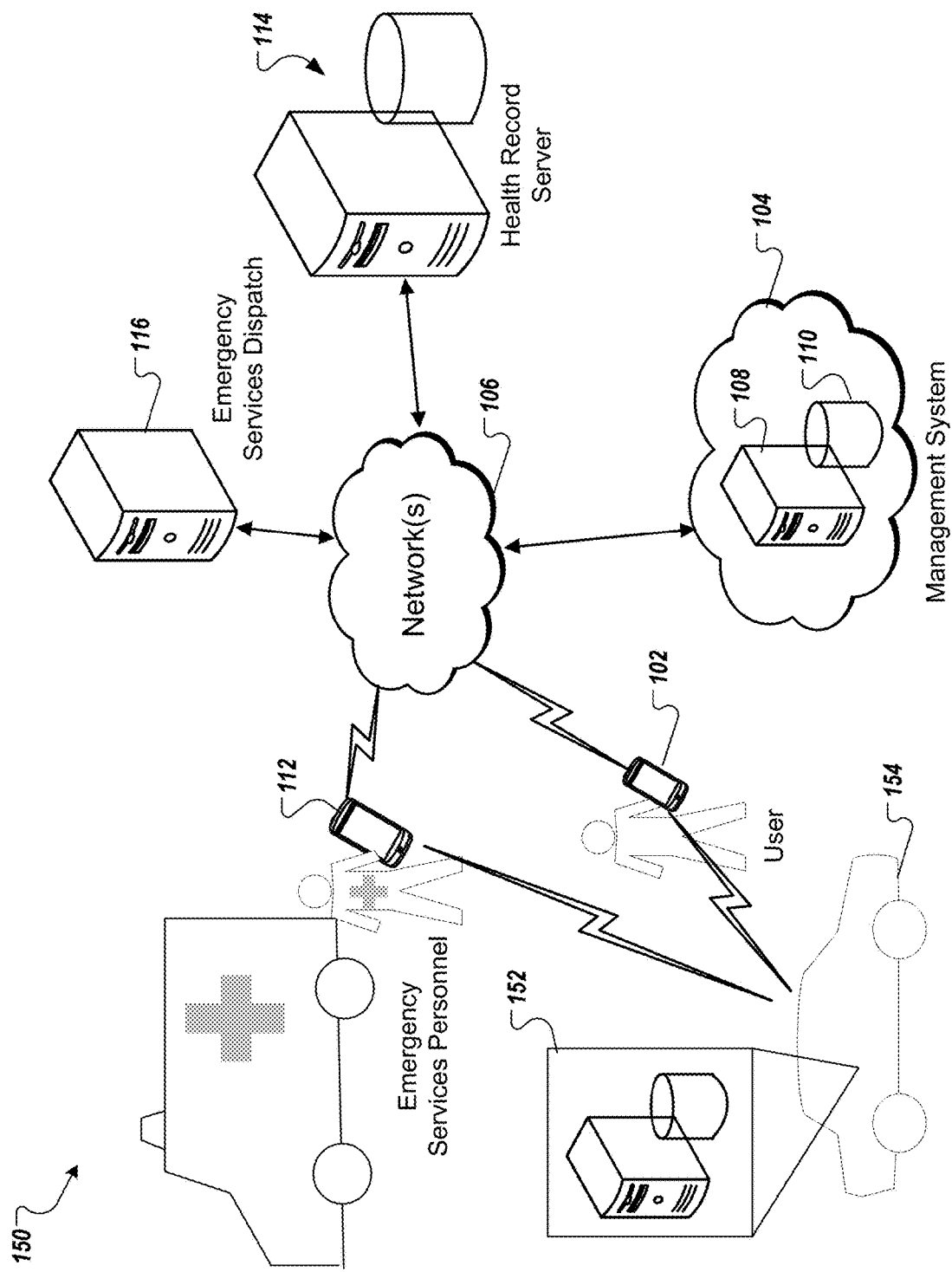

FIGS. 1A and 1B are diagrams of example systems that securely provide user health record data to emergency service personnel. Referring to FIG. 1A, the system 100 accesses a user's health record information after detecting that the user is engaged in an activity, makes the user's health record information available to emergency services personnel from a secure data storage container, and either provides the health record data to the emergency services personnel in response to detecting an indication that the user has been involved in an accident or makes the data inaccessible in response to an indication that the user is no longer engaged in the activity. For illustrative purposes, several elements illustrated in FIGS. 1A and 1B and described below are represented as monolithic entities. However, these elements each may include and/or be implemented on numerous interconnected computing devices and other components that are designed to perform a set of specified operations.

The system 100 includes a user computing device 102, which is in communication with a management system 104 over one or more networks 106. The user computing device 102 may be, for example, a cellular telephone, a smartphone, a tablet computer, a personal digital assistant (PDA), or a personal medical monitoring device. The management system 104 may include, for example, one or more servers 108 and one or more secure digital data storage devices 110. The networks 106 may include a wireless cellular network, a wireless local area network (WLAN) or Wi-Fi network, a Third Generation (3G) or Fourth Generation (4G) mobile telecommunications network, a private network such as an intranet, a public network such as the Internet, or any appropriate combination thereof. In addition, system 100 includes a first responder's computing device 112 configured to communicate with the user health record application on computing device 102 and the management system 104. The first responder's computing device 112 may be, for example, a cellular telephone, a smartphone, a tablet computer, a personal digital assistant (PDA), or a laptop computer.

In more detail, computing device 102 includes a user health record application configured to detect indications of activities performed by the user and to detect indications that the user has been involved in an accident. For example, the computing device 102 may be configured to sense motion inputs, for example, acceleration, rotation, and movement (e.g., via location services such as GPS or cellular triangulation). An indication of an activity or an accident may include, for example, a combination of motion inputs of various magnitudes received by the computing device 102. For instance, when a user is mountain biking the user health application may receive a series of acceleration/rotation inputs in rapid succession as the user rides along a trail and peddles his mountain bike in addition to GPS input indicating a speed at which the user is moving. Similarly, for example, when a user is riding in a car, the user health application may receive a relatively smooth acceleration input and GPS input indicating that the user is moving at a relatively high rate of speed. Likewise, an indication of an accident may be, for example, a large magnitude motion input or a rapid succession of large magnitude motion inputs followed by no motion input for a period of time.

Upon detecting the indication that the user is engaged in an activity, the user health record application on computing device 102 communicates with the management system 104 causing the management system 104 to make the user's health record available to a first responder. The management system server 108 may access health record data associated with the user from a health record server 114. Health record server 114 may be, for example, a digital health record repository (e.g., a Department of Health and Human Services medical recorded database, user provided health records, and/or third party health record data storage). The management system server 108 then may store the accessed health record data in a digital storage device 110. In some implementations, the digital storage device 110 may be cloud-based data storage. In some implementations, the management system server 108 may send the health record data to the computing device 102 and the health record data may be stored in a secure digital storage container on the computing device 102.

If the user health application detects an indication that the user is no longer engaged in the activity (e.g., the user has completed his mountain biking trip) and has not been involved in an accident, the user heath record application changes the state of the health record data such that it cannot be accessed. For example, in an implementation in which the health record data was stored on the computing device 102, the user health record application may remove the data from the device. Similarly, for example, in an implementation in which the health record data was stored in cloud-based data storage 110, the user health record application may communicate with the management system 104 causing the heath record data to be removed from the cloud-based data storage 110. By making the user's heath record data inaccessible when there is no potential need for the data (e.g., when the user is not engaged in a risky activity), the user heath record application is able to maintain a high-level of security for the user's health records.

If the user health application detects an indication that the user has been involved in an accident, the user health application provides the user's health record data to a first responder computing device 112. The first responder computing device 112 includes a first responder health record application configured to communicate with the user health record application and the management system 104. The first responder health record application may establish short-range communications with the user health record application on computing device 102. The user health record application may then authenticate the emergency services application prior to sending the user's health record data. Alternatively or in addition, the first responder health record application may authenticate itself to the management system 104 and the management system may provide the user's health record data to the first responder health record application, for instance, in an implementation in which the health record data was stored in cloud-based storage 110. Once the first responder health record application has received the user's health record data, the user health record application and/or the management system may change the state of the user's health record data stored on the computing device 102 or in cloud-based storage 110 such that it can no longer be accessed (e.g., the health record data may be removed). In some implementations, the state of the user health record data may be changed after a predetermined period of time from when the user health application received an indication of the accident (e.g., after several hours to ensure the data is made inaccessible in the event of a false accident indication).

In some implementations, although a user's health record data is made available, for example, by accessing the health record data from a health record server 112 and storing the health record data on the computing device 102, in cloud-based data storage 110, or in both locations, the health record data may not be accessed by any other computing devices unless the user health record application receives an indication that the user has been involved in an accident. In such an implementation, the occupant's health record data is made accessible to emergency service personnel only after receiving an indication that the user has been involved in an accident. Such an implementation ensures the user's privacy, the security of the user's health record data, and compliance with the Health Insurance Portability and Accountability Act (HIPPA), for example.

In some implementations, upon receipt of an indication that the user has been involved in an accident, the user health application may send a request for emergency services to an emergency services dispatch server 116 (e.g., a 911 server). The request for emergency services may include a GPS location of the user's computing device 102. In some implementation, the request for emergency services may be sent to the management system 104 and the management system 104 may coordinate the emergency services request with the emergency services dispatch server 116. In such an implementation, the request for emergency services may include the user's health record data, enabling emergency services personnel to review the user's health record in route to the accident scene.

In some implementations, the computing device 102 may be configured to monitor a user's vital signs (e.g., pulse, body temperature, etc.). In such an implementation, a user's vital signs may provide additional input data for the user health application to use as an indication that the user is engaged in an activity and as an indication that the user has been involved in an accident. In addition, upon receiving an indication that the user has been involved in an accident, the user health application may periodically send data indicating the user's vital signs to the management system 104 which may be made accessible to emergency personnel in route to the accident scene through the first responder health record application.

In some implementations, the user health record application may allow a user to manual indicate when the user is engaged in an activity and when the user is no longer engaged in the activity. For example, the manual indication may include a voice command, a touch screen input, or a keypad input. In addition, some implementations of the user health record application may allow a user to provide a manual indication that the user has been involved in an accident and requires emergency assistance. Likewise, the manual indication that a user has been involved in an accident may include a voice command, a touch screen input, or a keypad input, for example. In such an implementation, in response to the manual indication that the user has been involved in an accident, the user health record application may access the user's health record and make the accessed health record available and accessible to first responders. The user health record application also may request emergency services personnel from an emergency services dispatch server 116.

The management system 104 may, for example, be operated and maintained by, the producer of the user health record application, a health care provider or network of health care providers, a health record managing company, or other suitable third party. In some implementations, the health record server 112 may be part of the management system 104.

Referring to FIG. 1B, system 150 is similar to system 100 described above in reference to FIG. 1A, with the exception that system 150 includes a vehicle-based computing device 152 installed in a vehicle 154. The vehicle-based computing device 152 may be a module of the vehicle's 154 on-board computer system or a separate computing device, for example. The vehicle-based computing device 152 is configured to operate a user health record application and to communicate with other electronic devices using short-range communications (e.g., Bluetooth or NFC). In addition, the vehicle-based computing device 152 may be configured to exchange electronic communications with other computing devices through a network (e.g., a wireless cellular network, a wireless local area network (WLAN) or Wi-Fi network, a Third Generation (3G) or Fourth Generation (4G) mobile telecommunications network).

The vehicle-based computing device 152 detects an indication that an occupant has entered the vehicle 154 and identifies the occupant based on the indication. For example, the vehicle-based computing device 152 may establish short-range communication with the occupant's computing device 102 when the occupant enters the vehicle. The vehicle-based computing device 152 may then indicate to the occupant's computing device 102 that the vehicle-based computing device is operating a user health application and as such it is capable of storing the user's health record data. The health record application on the occupant's computing device 102 then may provide the occupant's identification information to the vehicle-based computing device 152.

Upon detecting the indication that the occupant has entered the vehicle 154 and identifying the occupant, the vehicle-based computing device 152 then access the occupant's health record data. In some implementations, the vehicle-based computing device accesses the occupant's health record data from the management system 104 through networks 106. The management system server 108 may access health record data associated with the user from a health record server 114. In some implementations, the vehicle-based computing device 152 may access the occupant's health record data by requesting that the computing device 102 retrieve the occupant's health record data through the management system 104.

The accessed health record data is then made available to emergency services personnel from a secure digital storage container. The accessed health record data may be stored in the vehicle-based computing device 152, for example. In some implementations, the management system server 108 then may store the accessed health record data in a digital storage device 110, for example. In some implementations, the digital storage device 110 may be cloud-based data storage.

If the vehicle-based computing device 152 detects an indication that the occupant has exited the vehicle 154 (e.g., based on loss of short-range communication with computing device 102 or based on a range to computing device 102 exceeding a threshold distance value) and that the vehicle 154 has not been involved in an accident, the vehicle-based computing device 152 changes the state of the health record data such that it cannot be accessed. For example, in an implementation in which the health record data was stored on the vehicle-based computing device 152, the user health record application may remove the data from the device. Similarly, for example, in an implementation in which the health record data was stored in cloud-based data storage 110, the vehicle-based computing device 152 may communicate with the management system 104 (either directly through networks 106 or by through the occupants computing device 102) causing the heath record data to be removed from the cloud-based data storage 110. By making the user's heath record data inaccessible when there is no potential need for the data (e.g., when the user is not engaged in a risky activity), the user heath record application is able to maintain a high-level of security for the user's health records.

If the vehicle-based computing device 152 detects an indication that the vehicle 154 has been involved in an accident (e.g., based on receiving an indication that airbags have deployed), the vehicle-based computing device 152 provides the occupant's health record data to a first responder computing device 112. The first responder computing device 112 includes an emergency services health record application configured to communicate with the vehicle-based computing device 152 and the management system 104. The emergency services health record application may establish short-range communications with the user health record application on vehicle-based computing device 152. The user health record application on the vehicle-based computing device 152 may then authenticate the emergency services application prior to sending the user's health record data. Alternatively or in addition, the emergency service application may authenticate itself to the management system 104 and the management system may provide the user's health record data to the emergency services application, for instance, in an implementation in which the health record data was stored in cloud-based storage 110. Once the emergency services application has received the user's health record data, the user health record application and/or the management system may change the state of the user's health record data stored on the vehicle-based computing device 152 or in cloud-based storage 110 such that it can no longer be accessed (e.g., the health record data may be removed). In some implementations, the state of the user health record data may be changed after a predetermined period of time from when the user health application received an indication of the accident (e.g., after several hours to ensure the data is made inaccessible in the event of a false indication).

In some implementations, although a user's health record data is made available, for example, by accessing the health record data from a health record server 112 and storing the health record data on the vehicle-based computing device 152, in cloud-based data storage 110, or in both locations, the health record data may not be accessed by any other computing devices unless the user health record application receives an indication that the vehicle 154 has been involved in an accident. In such an implementation, the occupant's health record data is made accessible to emergency service personnel only after receiving an indication that the vehicle 154 has been involved in an accident. Such an implementation ensures the user's privacy and the security of the user's health record data.

In some implementations, upon receipt of an indication that the vehicle 154 has been involved in an accident, the user health application on the vehicle-based based computing device 152 may send a request for emergency services to an emergency services dispatch server (e.g., a 911 server). The request for emergency services may include a GPS location of the vehicle 154. In some implementation, the request for emergency services may be sent to the management system 104 and the management system 104 may coordinate the emergency services request with the emergency services dispatch server 114. In such an implementation, the request for emergency services may include the user's health record data, enabling emergency services personnel to review the user's health record in route to the accident scene.

In some implementations, the vehicle-based computing device 152 may be configured to receive data indicating the occupant's vital signs (e.g., pulse, body temperature, etc.), for example, from the occupant's computing device 102. In such an implementation, upon receiving an indication that the user has been involved in an accident, the vehicle-based computing device 152 may periodically send data indicating the user's vital signs to the management system 104 which may be made accessible to emergency personnel in route to the accident scene through the first responder health record application.

Similar to system 100 above, the management system 104 may, for example, be operated and maintained by, the producer of the user health record application, a health care provider or network of health care providers, a health record managing company, or other suitable third party. In some implementations, the health record server 112 may be part of the management system 104.

FIGS. 2A-2D illustrate example graphical user interfaces (GUIs) of an example user health record application. In the example shown in FIG. 2A, the GUI 200, an example user health record application settings GUI, includes a name entry text box 202, a social security entry text box 204, an insurance provider entry text box 206, and an insurance policy number entry text box 208. The data entered in text boxes 202, 204, 206, and 208 may be used, for example, to identify the user and access the user's health record data or may be provided to the first responders with the health record data. In addition, the GUI 200 includes a photograph of the user 210. For example, the GUI 200 may allow the user to select a personal photograph from the user's digital photo library, to take a personal photograph using a camera located on the computing device 102, or the photograph may have been accessed as part of the user's health record data. The health record application may, in some implementations, provide the user's photograph to first responders along with the user's health record data to enable the first responders to identify the user from among multiple victims involved in an accident. GUI 200 also includes a selectable control 212 to establish a connection with a medical monitoring device, for example, to monitor the user's vital signs. In addition GUI 200 may allow a user to scroll up or down displaying additional user settings. For instance FIG. 2B, described below, illustrates additional example user settings for a user health record application that may be accessed by scrolling GUI 200.

In the example shown in FIG. 2B, GUI 220, a continuation of the user health application settings GUI, includes a selectable control 212 to establish a connection with a medical monitoring device, for example, to monitor the user's vital signs and a selectable list 222 of personal high risk activities (e.g., mountain biking, hiking, rock climbing, flying, biking, and boating). The user health record application may associate particular motion inputs with each activity listed in selectable list 222. The user health record application may then use a particular user's selection of one or more activities in the selectable list 222 to calibrate various activity indication profiles used to determine when a series of received motion/GPS inputs indicate that the user is engaged in an activity to trigger accessing the user's health record as described above in reference to FIG. 1A, for example.

In the example shown in FIG. 2C, the GUI 240 includes a notification window 242 informing a user that the health record application is attempting to link with a vehicle-based computing device 152. A notification window 242 may be displayed, for example, in relation to system 150 described above when an occupant enters or exits a vehicle 154. The notification window 242 may include various messages communicating to a user the status of the health record application and/or the status of communications with a vehicle-based computing device 152.

In the example shown in FIG. 2D, the GUI 260, an example health record application activity plan GUI, includes an activity dropdown selection box 262, a location drop down selection box 264, an expected return date/time dropdown selection box 266, and a pair of radio buttons 268. The activity plan GUI 260 allows a user to record a planned activity ahead of time. The user's activity plan may be used to help find the user in the event of an accident. For example, if the user is planning a hiking trip, the user may select hiking from the activity dropdown selection box 262, may enter or select the appropriate location (e.g., Chimney Rock in Shenandoah National Park) in the location dropdown selection box 264, and may enter or select the date and time the user expects to return in the expected return date/time dropdown selection box 266. Radio buttons 268 may allow a user to select between having the user health record application detect when the user begins the activity or manual indicating when the user begins the activity.

When the user begins the planned activity, the user health record application may cause the user's health record to be made available to first responders for the duration indicated by the user's activity plan regardless of the motion inputs received during that time period. In addition, the user heath record application may send the user's activity plan to the management system 104. This may be advantageous if the user will be in an area with minimal network connectivity, for example. Furthermore, if the user has not returned within a reasonable period from the expected return date (e.g., as indicated by GPS on the computing device 102) the management system 104 may request emergency services personnel by providing the user's activity plan and a last known GPS location of the computing device 102 in addition to making the user's health record information accessible to the first responders.

Figures 3A, 3B:
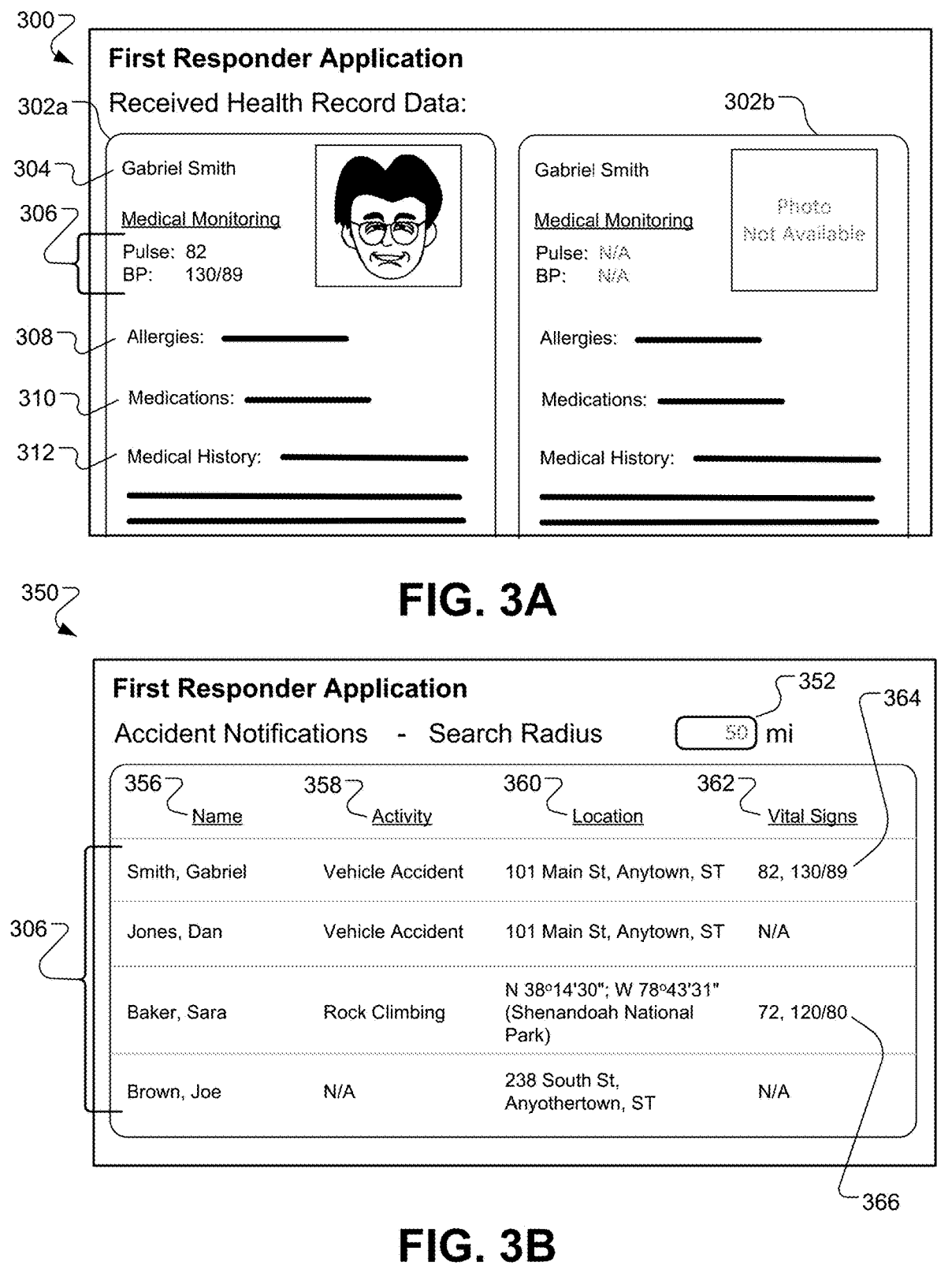

FIGS. 3A and 3B illustrate example GUIs of an example first responder health record application. In the example shown in FIG. 3A, the first responder health record application GUI 300 includes accessed health record data 302*a* and 302*b* for two individuals, Gabriel Smith 302*a* and Dan Jones 302*b*. Each health record 302*a* and 302*b* includes, for example, the name of the individual whose health record is displayed, the individual's vital signs 306 (e.g., pulse and blood pressure if the individual has a medical monitoring device paired with their user health record application), a list of the individual's allergies 308, a list of the individual's current medications 310, the individual's medical history 312, and, optionally, a photograph 314 of the individual. For example, Dan 302*b* has not yet incorporated a photograph 316 with his medical record data, however, Gabriel 302*a* has done so. In addition, the health record data 302*a* and 302*b* also may include information such as emergency contact data, (e.g., a spouse or parent's contact information), an individual's primary care provider, any specialists that the individual is seeing, and/or the individual's health insurance information.

In some implementations the health records 302*a* and 302*b* may have been accessed on-scene from a single vehicle in which each Gabriel and Dan were occupants (i.e., from a vehicle-based computing device 152), from two separate vehicles (e.g., Gabriel's car and Dan's truck), or from one or both individuals' personal computing device(s) 102. In some implementations, the first responders may have been able to access the health records 302*a* and 302*b* in route to the scene from cloud-based data storage 110.

In the example shown in FIG. 3B, the first responder health record application GUI 350 provides first responders with a selectable list of accident notifications for which health record data is available for at least one individual involved (e.g., a list as shown may be available in a cloud-based data storage implementation from the management system 104). GUI 350 includes an accident search radius dropdown box 352 and a list of accident notifications 354 within the selected search radius. Each entry in the list of accident notifications 354 includes a name of an individual for whom health record data is available 356, an activity in which the individual was involved before the accident 358, a location of the accident 360 (or last known location of the computing device 102 or 152), and the individual's vital signs 363. For example, Gabriel Smith (row 364) has been involved in a vehicle accident at 101 Main Street and has a medical monitoring device indicating that his pulse is 82 and his blood pressure is 130/89. As another example, Sara Baker (row 366) was involved in a rock climbing accident at the last known GPS location 38°14'30" N, 78°43'31" W (in Shenandoah National Park) and has a medical monitoring device indicating that her pulse is 72 and her blood pressure is 120/80.

Figure 4A:
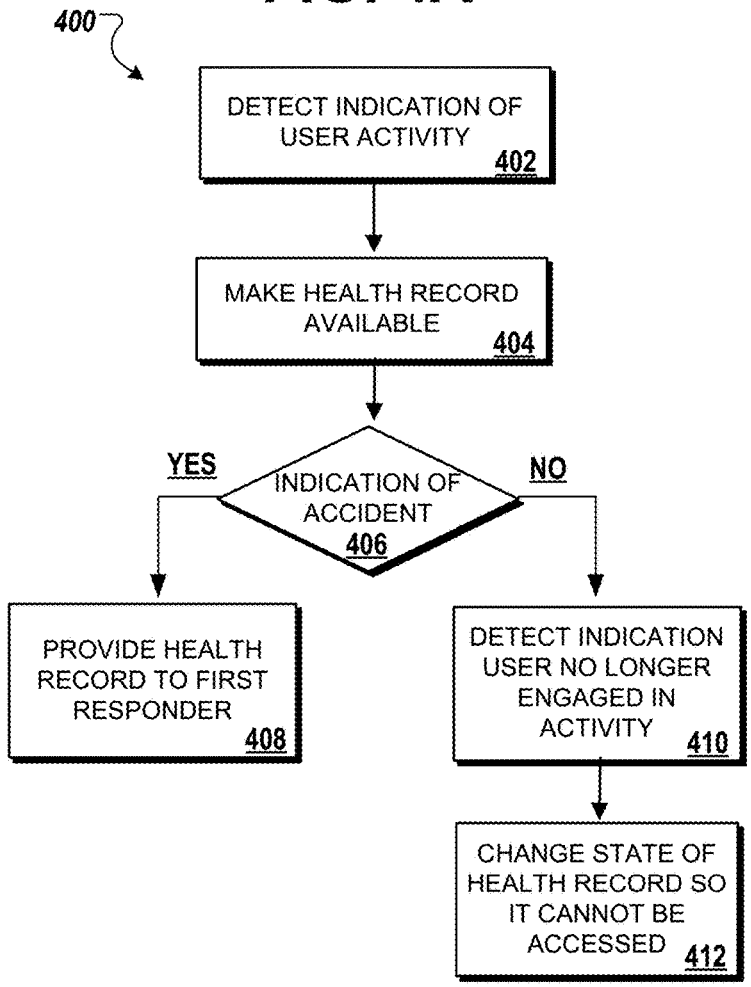
FIGS. 4A and 4B are flow charts of a process for providing a user's health record data to emergency service personnel.
Figure 4B:
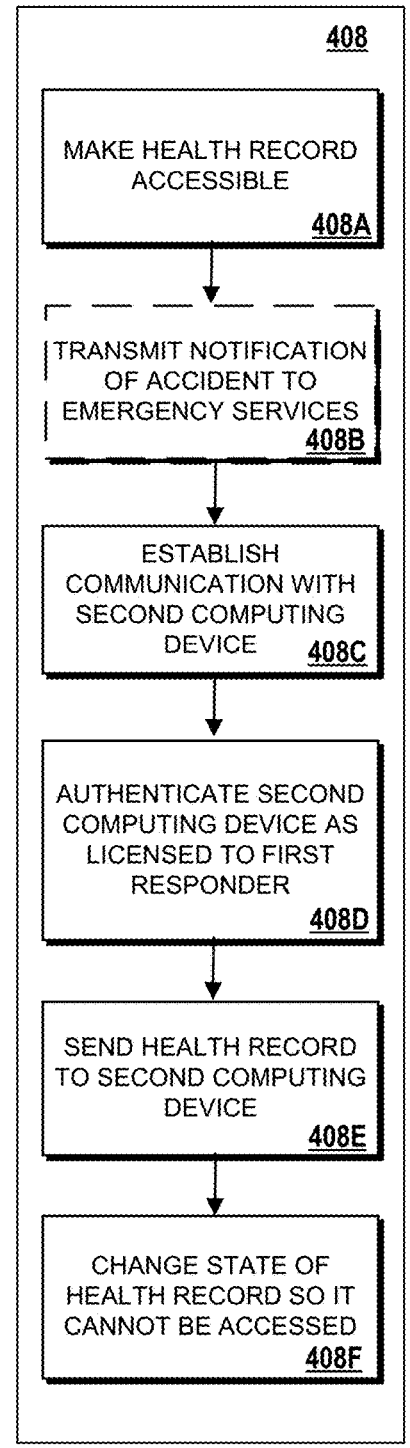

FIGS. 4A and 4B are flow charts of a process for providing a user's health record data to emergency service personnel. The process may be performed, in whole or in part, by a computing device such as, for example, computing device 102 or management server 104 of FIG. 1A. Referring to FIG. 4A, during process 400 a computing device detects an indication of a user activity (402). An indication of a user activity may, for example, include a combination of motion inputs of various magnitudes received by the computing device. Alternatively or in addition, an indication of a user activity may include, for example, GPS data such as a location, speed, and/or acceleration. The indication may be compared to one or more threshold values to determine whether the indication is an activity with a significant risk of accidents and for which a user's health record data should be made available. The threshold values may be, for example, based on statistical models describing the expected motion/GPS inputs for various activities. For example, a threshold value may be GPS indicated speed greater than 8 mph (e.g., the average human running speed). Such a speed may indicate that a user is biking, driving, etc. A GPS location indicating that the user is within a body of water may be, for example, a threshold value indicating that a user is boating. A threshold value also may be, for example, a series of acceleration/rotation inputs received in succession. In addition, the indication may be required to persist for a specified period to avoid false positive indications. For example, the motion input received while a user is mountain biking may be similar to the motion input received if the computing device is dropped. To avoid identifying a drop as a user activity, the computing device may require the motion input to persist for several seconds before determining that the motion input is a user activity.

In some implementations, it may be possible to match activity indications to specific activities, for example, based on activity profiles. A GPS location placing the user within a body of water may, for example, be recognized as a boating activity. In addition, some implementations may allow the user to generate custom activity threshold value profiles and calibrate the computing device to recognize indications of activities customized to the user by, for example, performing an activity while the computing device receives and records various motion and GPS inputs and then associating the inputs the type of activity. In some implementations, the computing device may allow a user to manually indicate the start of a user activity (e.g., via a voice command, touch screen input, keypad input, or other appropriate input).

Based on detecting an indication of a user activity, the computing device makes a user's health record data available to first responders (404). The computing device may, for example, have to access the user's health record data from a health record database or digital repository. The computing device then may temporarily store the user's health record data in format and location such that the health record data is more readily available. For example, the computing device may store the health record data in a secure digital storage container on the computing device itself. Alternatively or in addition, the computing device may cause the health record data to be stored in a cloud-based secure digital storage container.

If the computing device detects an indication of an accident (406), the computing device provides the health record data to the first responder (408). An indication of an accident may include, for example, a combination of motion inputs of various magnitudes received by the computing device. Alternatively or in addition, an indication of a user activity may include, for example, GPS data such as a location, speed, and/or acceleration. The indication may be compared to one or more accident threshold values to determine whether the inputs may properly be identified as an accident. The accident threshold values may be, for example, based on statistical models describing the expected motion/GPS inputs for various types of accidents. In addition, the accident threshold values may be modified based on a particular activity in which a user is engaged. For example, motion/GPS inputs occurring during a vehicle accident would be expected to be more severe than those occurring during a biking accident. In addition, a minor fender bender may, for example, result in motion/GPS inputs that equivalent to those received during a biking accident. False accident indication may be avoided by modifying the accident threshold values when a user is indicated to be engaged in an activity associated with more sever accidents, for example, riding in an automobile. Similarly, accidents that otherwise may not be detected may be more readily or more often detected by modifying the accident threshold values when a user is indicated to be engaged in an activity associated with less sever accidents, for example, riding a bicycle.

In some implementations, the computing device may include or be paired with a medical monitoring device. In such implementations, an indication of an accident may include an indication that one or more of the user's vital signs have crossed a threshold value (e.g., an unusually low pulse, or an unusual blood pressure). In addition, in some implementations the computing device may allow a user to manually indicate that the user has been involved in an accident (e.g., via a voice command, touch screen input, keypad input, or other appropriate input). In such implementations (i.e., implementations including a vital sign based accident indication and/or implementations allowing a user to manually indicate that an accident has occurred), it may be desirable for the computing device to be receptive to the accident indication even when the user has not been identified as being engaged in an activity. In these implementations, based on receiving a vital sign based accident indication or a manual accident indication; the computing device may cause the user's health record to be made available to first responders (see step 404 above).

Referring now to FIG. 4B, to provide the health record to the first responder (408), the computing device makes the health record data accessible to the first responder (408A). For example, until an indication of an accident is received, the health record data may be stored in such a manner or format that it may not be accessed by other computing devices or the user (e.g., it may be stored with appropriate privacy settings, stored in an encrypted format, flagged as private, and/or stored as a hidden file). After an indication of an accident is detected, the state of the health record data may be appropriately changes such that the health record data is made accessible to first responders. In some implementations, the health record data may be locked in the secure digital storage container(s) such that it will not be inappropriately deleted or modified prior to being accessed by first responders.

Optionally, the computing device transmits a notification of the accident to emergency services (408B). In some implementations, the computing device may, upon receiving an indication of an accident, transit a request for emergency services to an appropriate emergency services dispatch location. The request may include, for example, the location of the computing device or last known location (e.g., in the event that the computing device is damaged in the accident).

The computing device establishes communication with a second computing device (408C). Communications between the two computing devices may be established, for example, via short-range wireless communication (e.g., Bluetooth or NFC) and/or through a network (e.g., a wireless cellular network, a WLAN or Wi-Fi network, a 3G or 4G mobile telecommunications network). The computing device then may authenticate the second computing device as being a licensed first responder computing device (408D). For example, a first responder health record application operating on the second computing device may send authentication information to a user computing device which may be validated by a corresponding user health record application operating on the user computing device. Similarly, for example, a first responder health record application operating on the second computing device may send authentication information to a management system computing device which may be validated by a corresponding management health record application operating on the management system computing device.

The computing device sends the user's health record data to the authenticated second computing device (408E). Upon successfully authenticating the second computing device the health record data is sent to the second computing device for display in a first responder health record application, for example. The computing device changes the state of the user's health record data so that the health record data cannot be accessed (408F). In order to, for example, maximize the security of a user's health record data, the computing device changes the state of the stored health record data so that the health record data can no longer be accessed. The computing device may change the state of the health record data by securely removing the health record data from the secure digital storage container, for example, by deleting the health record data or by overwriting the user's health record data with zeros. The computing device may change the state of the health record data after the expiration of a specified period of time from when the accident indication was received (e.g., two hours after receiving the accident indication). In some implementations, the computing device may change the state of the health record data after it has been accessed by an authenticated second computing device, for example.

Referring again to FIG. 4A, if the computing device does not detect an indication of an accident (406), the computing device may detect an indication that the user is no longer engaged in the activity (410). An indication that a user is no longer engaged in the activity may include, for example, the cessation of the previously received indication of the activity for a specified period of time. For example, the computing device may require that motion/GPS input indicating the activity must cease for several minutes to be considered an indication that the user is no longer engaged in the activity. For instance, if a user were biking in a city and stopped at a red street light, it would not be appropriate to identify the brief cessation of motion/GPS input as an indication that the user is no longer engaged in the activity. However, when the user arrives at her destination and the biking motion/GPS input ceases for an extended period of time it would be appropriate to identify the cessation of motion/GPS input as an indication that the user is no longer engaged in the activity.

Upon detecting the indication that the user is no longer engaged in the activity, the computing device changes the state of the user's health record data so that the health record data cannot be accessed (412). In order to, for example, maximize the security of a user's health record data, the computing device changes the state of the stored health record data so that the health record data can no longer be accessed. The computing device may change the state of the health record data by securely removing the health record data from the secure digital storage container, for example, by deleting the health record data or by overwriting the user's health record data with zeros.

FIGS. 5A and 5B are flow charts of a process for providing a user's health record data to emergency service personnel. The process may be performed, in whole or in part, by a computing device such as, for example, computing device 152 or management server 104 of FIG. 1B. Referring to FIG. 5A, during process 500 a computing device detects an indication that an occupant has entered a vehicle (502) and identifies the occupant (504). The computing device may establish short-range communication (e.g., Bluetooth or NFC) with the occupant's personal computing device (e.g., a cellular telephone, smartphone, personal digital assistant, medical monitoring device, or other appropriate device) when the occupant enters the vehicle. The computing device then may indicate to the occupant's personal computing device that the computing device is capable of storing the occupant's health record data. The computing device then may receive identification information for the occupant form the occupant's personal computing device.

In some implementations, the indication that the occupant has entered the vehicle and the data identifying the occupant may include a digital identification embedded in a key to start the vehicle, for example. The computing device may receive the occupant's digital identification when the occupant starts the vehicle. In some implementations the indication that the occupant has entered the vehicle and the data identifying the occupant may include a machine readable tag (e.g., a radio frequency identification (RFID) tag or other appropriate device) including a digital identification of the occupant. For example, the computing device may read occupant's digital identification from the machine readable tag (e.g., a card in the occupant's wallet or a tag on the occupant's key chain) when the occupant enters the vehicle.

The computing device accesses the occupant's health record data (506), and makes a user's health record data available to first responders (508). The computing device may, for example, have to access the user's health record data from a health record database or digital repository. The computing device then may temporarily store the user's health record data in a format and a location such that the health record data is more readily available. For example, the computing device may store the health record data in a secure digital storage container on the computing device itself. Alternatively or in addition, the computing device may cause the health record data to be stored in a cloud-based secure digital storage container If the computing device detects an indication of an accident (510), the computing device provides the health record data to the first responder (512). An indication of an accident may include, for example, an indication that the vehicle's airbag has deployed or a combination of motion inputs of various magnitudes received by the computing device. Alternatively or in addition, an indication of a user activity may include, for example, GPS data such as a location, speed, and/or acceleration. The indication may be compared to one or more accident threshold values to determine whether the inputs may properly be identified as an accident. The accident threshold values may be, for example, based on statistical models describing the expected motion/GPS inputs for various types of accidents.

In some implementations, the computing device may include or be paired with a medical monitoring device. In such implementations, an indication of an accident may include an indication that one or more of the user's vital signs have crossed a threshold value (e.g., an unusually low pulse, or an unusual blood pressure). In addition, in some implementations the computing device may allow a user to manually indicate that the user has been involved in an accident (e.g., via a voice command, touch screen input, keypad input, or other appropriate input). In such implementations (i.e., implementations including a vital sign based accident indication and/or implementations allowing a user to manually indicate that an accident has occurred), it may be desirable for the computing device to be receptive to the accident indication even when the user has not been identified as being engaged in an activity. In these implementations, based on receiving a vital sign based accident indication or a manual accident indication; the computing device may cause the user's health record to be made available to first responders (see step 506 above).

Referring now to FIG. 5B, to provide the health record to the first responder (512), the computing device makes the health record data accessible to the first responder (515A). For example, until an indication of an accident is received, the health record data may be stored in such a manner or format that it may not be accessed by other computing devices or the user (e.g., it may be stored with appropriate privacy settings, stored in an encrypted format, flagged as private, and/or stored as a hidden file). After an indication of an accident is detected, the state of the health record data may be appropriately changes such that the health record data is made accessible to first responders. In some implementations, the health record data may be locked in the secure digital storage container(s) such that it will not be inappropriately deleted or modified prior to being accessed by first responders.

Optionally, the computing device transmits a notification of the accident to emergency services (512B). In some implementations, the computing device may, upon receiving an indication of an accident, transit a request for emergency services to an appropriate emergency services dispatch location. The request may include, for example, the location of the computing device or last known location (e.g., in the event that the computing device is damaged in the accident).

The computing device establishes communication with a second computing device (512C). Communications between the two computing devices may be established, for example, via short-range wireless communication (e.g., Bluetooth or NFC) and/or through a network (e.g., a wireless cellular network, a WLAN or Wi-Fi network, a 3G or 4G mobile telecommunications network). The computing device then may authenticate the second computing device as being a licensed first responder computing device (512D). For example, a first responder health record application operating on the second computing device may send authentication information to a user computing device which may be validated by a corresponding user health record application operating on the user computing device. Similarly, for example, a first responder health record application operating on the second computing device may send authentication information to a management system computing device which may be validated by a corresponding management health record application operating on the management system computing device.

The computing device sends the user's health record data to the authenticated second computing device (512E). Upon successfully authenticating the second computing device the health record data is sent to the second computing device for display in a first responder health record application, for example. The computing device changes the state of the user's health record data so that the health record data cannot be accessed (512F). In order to, for example, maximize the security of a user's health record data, the computing device changes the state of the stored health record data so that the health record data can no longer be accessed. The computing device may change the state of the health record data by securely removing the health record data from the secure digital storage container, for example, by deleting the health record data or by overwriting the user's health record data with zeros. The computing device may change the state of the health record data after the expiration of a specified period of time from when the accident indication was received (e.g., two hours after receiving the accident indication). In some implementations, the computing device may change the state of the health record data after it has been accessed by an authenticated second computing device, for example.

Referring again to FIG. 5A, if the computing device does not detect an indication of an accident (510), the computing device may detect an indication that the occupant has exited the vehicle (514). For example, the computing device may lose short-range communications with the occupant's personal computing device or the range between the computing device and the occupants personal computing device may exceed a specified threshold distance (e.g., based on a measured received signal strength). In some implementations, the indication may include an indication that the occupant has turned the vehicle off or removed a key from the ignition, for example.

Upon detecting the indication that the occupant has exited the vehicle, the computing device changes the state of the user's health record data so that the health record data cannot be accessed (516). In order to, for example, maximize the security of a user's health record data, the computing device changes the state of the stored health record data so that the health record data can no longer be accessed. The computing device may change the state of the health record data by securely removing the health record data from the secure digital storage container, for example, by deleting the health record data or by overwriting the user's health record data with zeros.

The techniques described herein can be implemented in digital electronic circuitry, or in computer hardware, firmware, software, or in combinations of them. The techniques can be implemented as a computer program product, i.e., a computer program tangibly embodied in an information carrier, e.g., in a machine-readable storage device, in machine-readable storage medium, in a computer-readable storage device or, in computer-readable storage medium for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques can be performed by one or more programmable processors executing a computer program to perform functions of the techniques by operating on input data and generating output. Method steps can also be performed by, and apparatus of the techniques can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, such as, magnetic, magneto-optical disks, or optical disks. Information carriers suitable for embodying computer program instructions and data include all forms of non-volatile memory, including by way of example semiconductor memory devices, such as, EPROM, EEPROM, and flash memory devices; magnetic disks, such as, internal hard disks or removable disks; magneto-optical disks; and CD-ROM and DVD-ROM disks. The processor and the memory can be supplemented by, or incorporated in special purpose logic circuitry.

A number of implementations of the techniques have been described. Nevertheless, it will be understood that various modifications may be made. For example, useful results still could be achieved if steps of the disclosed techniques were performed in a different order and/or if components in the disclosed systems were combined in a different manner and/or replaced or supplemented by other components. Accordingly, other implementations are within the scope of the following claims.

The invention claimed is:

1. A computer implemented method executed by a first computing device, the method comprising:
   detecting, by the first computing device, a first set of sensor data collected by one or more sensors, the first set of sensor data indicative of a first motion of a user;
   determining, by the first computing device, that the user is presently engaged in a high risk activity based on a statistical model and the first set of sensor data;
   based on determining that the user is presently engaged in the high risk activity, generating, by the first computing device and at a first time, a secure digital container that temporarily stores health record information associated with the user on the first computing device;
   determining, by the first computing device and at a second time, that an accident has occurred based on a second set of sensor data collected by the one or more sensors, the second set of sensor data indicative of a second motion of the user; and
   based on determining that the accident has occurred:
      establishing, by the first computing device, a short-range connection with a second computing device, and
      providing, by the first computing device, access to the secure digital container over the short-range connection;
   determining, by the first computing device and at a third time, that the user is no longer engaged in the high risk activity; and
   based on determining that the user is no longer engaged in the high risk activity at the third time, terminating, by the first computing device, access to the secure digital container over the short-range connection.

2. The method of claim 1, wherein:
   determining that the accident has occurred comprises determining that the accident has occurred based on the second set of sensor data; and
   the second computing device is registered to a first responder.

3. The method of claim 2, wherein terminating access to the secure digital container comprises:
   changing a state of the health record information such that the health record information can be accessed from the secure digital container;
   authenticating the second computing device as being registered to the first responder;
   in response to authenticating the second computing device, sending data representing the health record information of the secure digital container to the second computing device; and changing the state of the health record information such that the health record information can no longer be accessed from the secure digital container after the third time.

4. The method of claim 1, further comprising:
comparing the second set of sensor data to statistical model data, the statistical model data being indicative of expected sensor data for accidents; and
wherein determining that the accident has occurred comprises determining, based on comparing the second set of sensor data to the statistical model data, that the accident has occurred.

5. The method of claim 1, wherein determining that the user is presently engaged in a high risk activity comprises comparing an activity parameter specified in the first set of sensor data to an activity threshold value.

6. The method of claim 5, wherein the first set of sensor data comprises motion data from a motion sensor included in the one or more sensors.

7. The method of claim 5, wherein the first set of sensor data comprises GPS data.

8. The method of claim 5, wherein the activity threshold value is obtained from an activity profile that includes stored sensor data from a previous time that the user had performed the high risk activity.

9. The method of claim, 5 wherein the activity threshold value is determined based on a statistical model describing expected data from the one or more sensors.

10. The method of claim 1, further comprising determining that the high risk activity is a particular type of activity based on the first set of sensor data matching data associated with an activity profile of the particular type of activity.

11. The method of claim 1, wherein determining that the user is presently engaged in a high risk activity comprises determining that the first set of sensor data has persisted for a predetermined period of time.

12. A non-transitory computer readable medium storing instructions that, when executed by at least one processor, cause the at least one processor to perform operations comprising:
detecting, by a first computing device, a first set of sensor data collected by one or more sensors, the first set of sensor data indicative of a first motion of a user;
determining, by the first computing device, that the user is presently engaged in a high risk activity based on a statistical model and the first set of sensor data;
based on determining that the user is presently engaged in the high risk activity, generating, by the first computing device and at a first time, a secure digital container that temporarily stores health record information associated with the user on the first computing device;
determining, by the first computing device and at a second time, that an accident has occurred based on a second set of sensor data collected by the one or more sensors, the second set of sensor data indicative of a second motion of the user; and
based on determining that the accident has occurred:
establishing, by the first computing device, a short-range connection with a second computing device, and
providing, by the first computing device, access to the secure digital container over the short-range connection;
determining, by the first computing device and at a third time, that the user is no longer engaged in the high risk activity; and
based on determining that the user is no longer engaged in the high risk activity at the third time, terminating, by the first computing device, access to the secure digital container over the short-range connection.

13. The medium of claim 12, wherein:
determining that the accident has occurred comprises determining that the accident has occurred based on the second set of sensor data; and
the second computing device is registered to a first responder.

14. The medium of claim 13, wherein terminating access to the secure digital container comprises:
changing a state of the health record information such that the health record information can be accessed from the secure digital container;
authenticating the second computing device as being registered to the first responder;
in response to authenticating the second computing device, sending data representing the health record information of the secure digital container to the second computing device; and
changing the state of the health record information such that the health record information can no longer be accessed from the secure digital container after the third time.

15. The medium of claim 12, wherein the operations further comprise:
comparing the second set of sensor data to statistical model data, the statistical model data being indicative of expected sensor data for accidents; and
wherein determining that the accident has occurred comprises determining, based on comparing the second set of sensor data to the statistical model data, that the accident has occurred.

16. The medium of claim 12, wherein determining that the user is presently engaged in a high risk activity comprises comparing an activity parameter specified in the first set of sensor data to an activity threshold value.

17. The method of claim 1, further comprising:
providing, to a server, an instruction to store the health record information associated with the user in the secure digital container.

* * * * *